United States Patent [19]

Ungerer et al.

[11] Patent Number: 5,536,474
[45] Date of Patent: Jul. 16, 1996

[54] SYSTEM FOR TRANSFERRING SAMPLES UNDER PRESSURE

[75] Inventors: Philippe Ungerer, Creteil; Gérard Moracchini, Andilly; José Sanchez, Viarmes, all of France

[73] Assignee: Institut Francais du Petrole, Rueil Malmaison, France

[21] Appl. No.: 258,384

[22] Filed: Jun. 10, 1994

[30] Foreign Application Priority Data

Jun. 11, 1993 [FR] France .................................. 93 07077

[51] Int. Cl.[6] ...................................................... B01L 3/00
[52] U.S. Cl. .............................. 422/100; 422/81; 422/83; 422/102; 73/64.56; 73/864.62
[58] Field of Search ............................. 422/100, 81, 102, 422/83; 436/174, 180, 181; 73/64.56, 869.62

[56] References Cited

U.S. PATENT DOCUMENTS

| | | | |
|---|---|---|---|
| 3,892,130 | 7/1975 | Winget et al. | 73/864.62 |
| 5,088,335 | 2/1992 | La Freniere et al. | 73/864.62 |
| 5,213,763 | 5/1993 | Richecoeur et al. | 422/100 |

FOREIGN PATENT DOCUMENTS 0473472  3/1992  European Pat. Off. .

*Primary Examiner*—Jill Warden
*Assistant Examiner*—Jan M. Ludlow
*Attorney, Agent, or Firm*—Antonelli, Terry, Stout & Kraus

[57] ABSTRACT

Fluids kept under high pressure in one or several balancing cells (C1, C2) inside a thermostat-controlled enclosure (14) at about 200° C. are extracted by introducing into the enclosure a sampling cell (1) capable of withstanding pressures of the order of 150 MPa, fastening cell (1) to a connection element (24) linked to balancing cells, taking samples and removing the cell from the thermostat-controlled enclosure, with all of these operations being easily conducted from outside. After possible weighing of the sampling cell, a transfer device thereafter allows the sampling cell to be communicated with measuring and analysis devices such as a gasometer associated with a separating bottle, a solvent injection means, etc. Operations are synchronized by a programmed microcomputer (MC). The preferred application is processing geological samples.

22 Claims, 4 Drawing Sheets

SYSTEM FOR TRANSFERRING SAMPLES UNDER PRESSURE

FIELD OF THE INVENTION

The present invention relates to a system for transferring fluid samples under very high pressure and at a very high or very low temperature, according to the type of applications, in order to determine some of the thermodynamic properties thereof.

The system according to the invention is useful notably within surveys relating to the thermodynamic properties of samples originally taken in boreholes down in subsurface reservoirs, and placed, at the surface, under pressure and temperature conditions which reproduce the conditions prevailing in the sampling places. The object of the measurements is notably to assess the petroleum effluent content of the samples.

BACKGROUND OF THE INVENTION

Thermodynamic properties are calculated by using composition models in which data obtained by analysis of the samples are integrated and by varying certain parameters such as pressure and temperature for example, from values reproducing those existing at the bottom of the bore hole to those prevailing at the surface. Analysis methods of this type allow important properties to be measured, such as the "bubbles point" indicating the appearance of a gas phase in the sample tested, the compressibility coefficient, the density, the GOR (gas/oil ratio), etc, as it is known to specialists.

A device intended for conducting measuring operations on samples is for example described in the French patent application 2,666,415 filed by the applicant. It includes a thermostatically-controlled enclosure containing two cells consisting of two cylindrical chambers defined respectively by two mobile pistons, driving means for moving the two pistons in an independant or coordinated way and a microprocessor drive system. This device allows a whole series of operations to be achieved while keeping the samples placed in the chambers under pressure and temperature conditions analogous to those prevailing in the bottom of a bore hole.

Conducting certain measuring operations requires the possibility of taking a fraction of the sample volumes contained in the study cells inside the thermostat-controlled enclosure. In order to facilitate handlings and to improve measurement precision, it is important to respect certain conditions:

Sampling must preferably be achieved under the pressure and temperature conditions prevailing in the thermostat-controlled enclosure, the sampling cell must therefore be introduced easily into the enclosure and simply coupled to the balancing cell containing the substance to be taken, before it is removed in the same way.

The volume of the sample taken and the mass thereof must be known with precision in order to be able to measure easily the density thereof, and it has to be transferable almost totally to other measuring devices.

Furthermore, the sampling cell must be easily detachable so as to allows visual checks.

The operation of withdrawal of the fraction and of transfer to a measuring device such as a gasometer must be performed automatically so that set values may be easily accomplished.

SUMMARY OF THE INVENTION

The transfer system according to the invention allows samples to be taken easily and precisely in one or several balancing cells arranged in a thermostat-controlled enclosure kept at a high or very low temperature, according to applications, and transferred to analysis devices in order to determine some of the thermodynamic properties thereof, while achieving the specifications stated above.

The invention comprises in combination:

A sampling cell for containing fluids under high pressure, including a body provided with a cavity of variable volume and a first valve a fixed connection element arranged in the thermostat-controlled enclosure close to an opening provided in a wall thereof and communicating with the balancing cell by means of a second valve control, which may be operated from outside the thermostat-controlled enclosure, for introducing and fastening the sampling cell against the connection element so as to allows controlled communication between the cavity and the balancing cell;

an operating assembly integral with the first connection element for varying the volume of the cavity when the sampling cell is fastened to the first connection element; and a transfer device for controlling fluid transfers between the sampling cell and devices for analyzing thermodynamic properties.

According to an embodiment of the invention, the cavity inside the body of the sampling cell is defined by a mobile piston, which may be moved through an adjustable position, the piston being integral with a flange associated with guide elements for guidance with respect to the body of the cell which includes a head provided with means for fastening into the connection element.

The first operating assembly may include for example a motor exterior to the thermostat-controlled enclosure and operating means driven by the motor for controlling the displacement of the piston of the sampling cell, guide rods associated with a transmission block connected to the motor for rotating the rods, and means moving linearly along the rods, for driving in translation the piston of the sampling cell.

The control means include for example a second valve associated with the first connection element and accessible from outside the thermostat-controlled enclosure, for controlling the communication between the sampling cell and the balancing cell.

The transfer device between the sampling cell and the thermodynamic property analysis devices includes for example a second operating assembly consisting of a support associated with a second connection element for fastening the head of the sampling cell, including at least one or several valves for controlling the transfer of fluids between the sampling cell and a reception assembly (such as a gasometer associated with a separating bottle, and alternitively means for controlling communication between the gasometer and a vacuum pump), alternitively at least one other valve for controlling communication between the sampling cell and a solvent injection element, and means for abutting against the piston of this cell.

The transfer device may also include at least one valve for controlling transfers between the injection element, the sampling cell and the reception assembly.

The means for introducing and for fastening the sampling cell against the first connection element preferably include an opening whose dimensions are those of the sampling cell, provided in the wall of the thermostat-controlled enclosure opposite the connection element, with the opening being fitted with a removable cover, and operating keys for the transportation of the sampling cell.

The system preferably includes a control processor for synchronizing the transfer of fluids at a substantially constant pressure between the balancing cell and the sampling cell and or the sampling cell and the analysis devices.

BRIEF DESCRIPTION OF THE DRAWINGS

Other features and advantages of the system according to the invention will be clear from reading the description hereafter of embodiments given by way of non limitative examples, with reference to the accompanying drawings in which.

DESCRIPTION OF THE PREFERRED EMBODIMENTS

Figure 1:
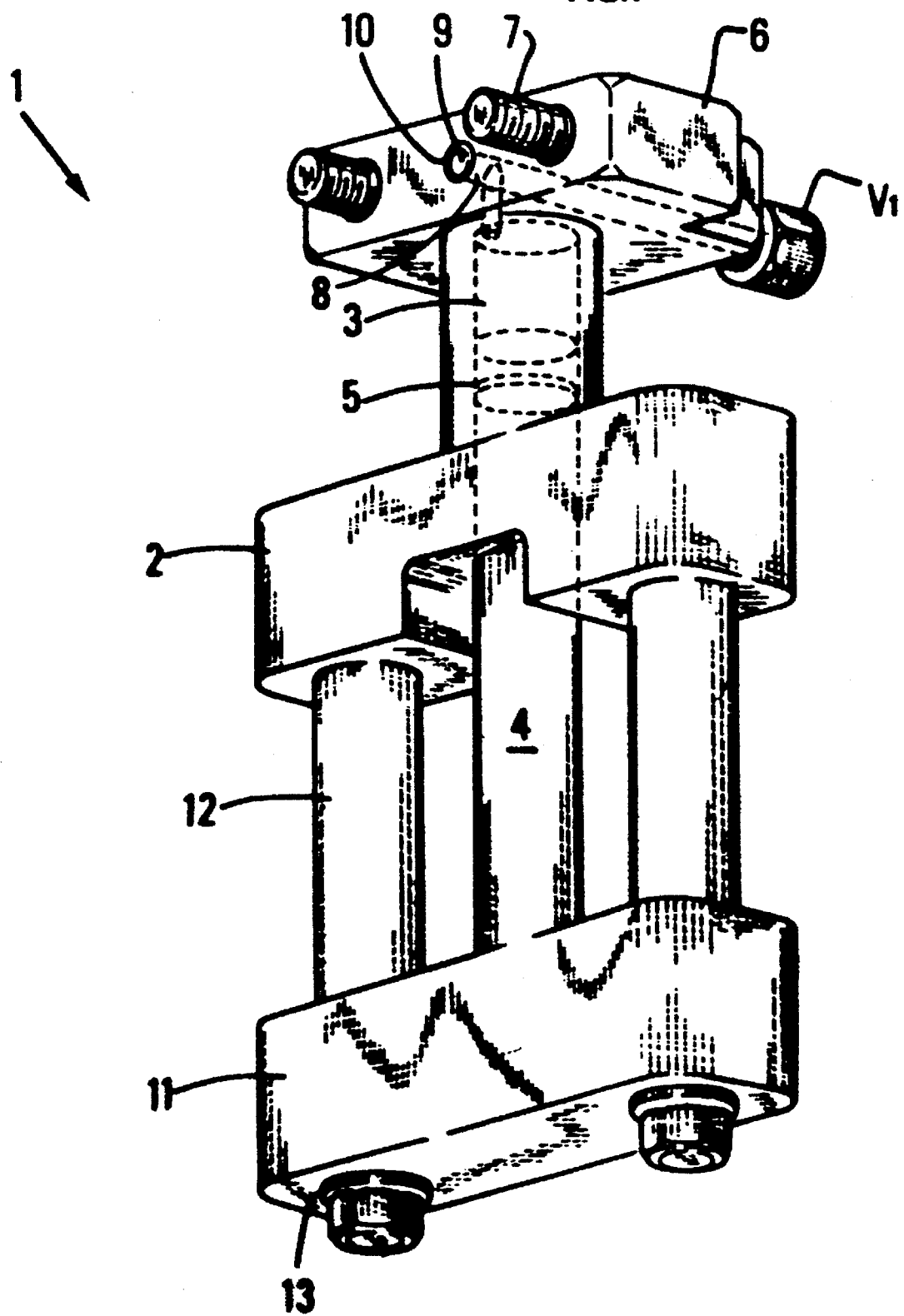
FIG. 1 shows an embodiment of the sampling cell.

The transfer system according to the invention includes a sampling cell 1 consisting of a body 2 provided with a cylindrical cavity 3 and with a piston 4 having a length greater than that of cavity 3. The piston is provided with seals 5 for containing gas within a wide range of temperatures (−100° C. to 200° C. for example) and of pressures (0–150 MPa). Piston 4 slides within cavity 3 between a first position of engagement substantially in contact with the bottom of the cavity and a second adjustable position of recoil. The maximum volume of cavity 3 in the second position of recoil is on the order of 2 cm³ in a preferred embodiment. On the side of the bottom of cavity 3, cell 1 includes a head 6 traversed by two screws 7 and by a fine bent channel 8. Channel 8 emerges outside body 2 through a port 9 fitted with a circular groove for retaining an O seal ring 10. A needle valve V1 is interposed in channel 8 for controlling the communication of cavity 3 with the outside. The valve V1 is so arranged that the volume of the part of the channel between the bottom of cavity 3 and the needle (clearance volume) is extremely small, of the order of 1 mm³, and therefore less than a thousandth of the maximum volume of the cavity. A flange 11 is fastened to piston 4 outside the cavity. The flange 11 may slide along two rods 12 integral with body 2 having length sufficient to allow a displacement of piston 4 until the maximum position of recoil thereof is reached. This piston is adjusted by interposing washers 13 between the head of rods 12 and flange 11.

Figure 2:
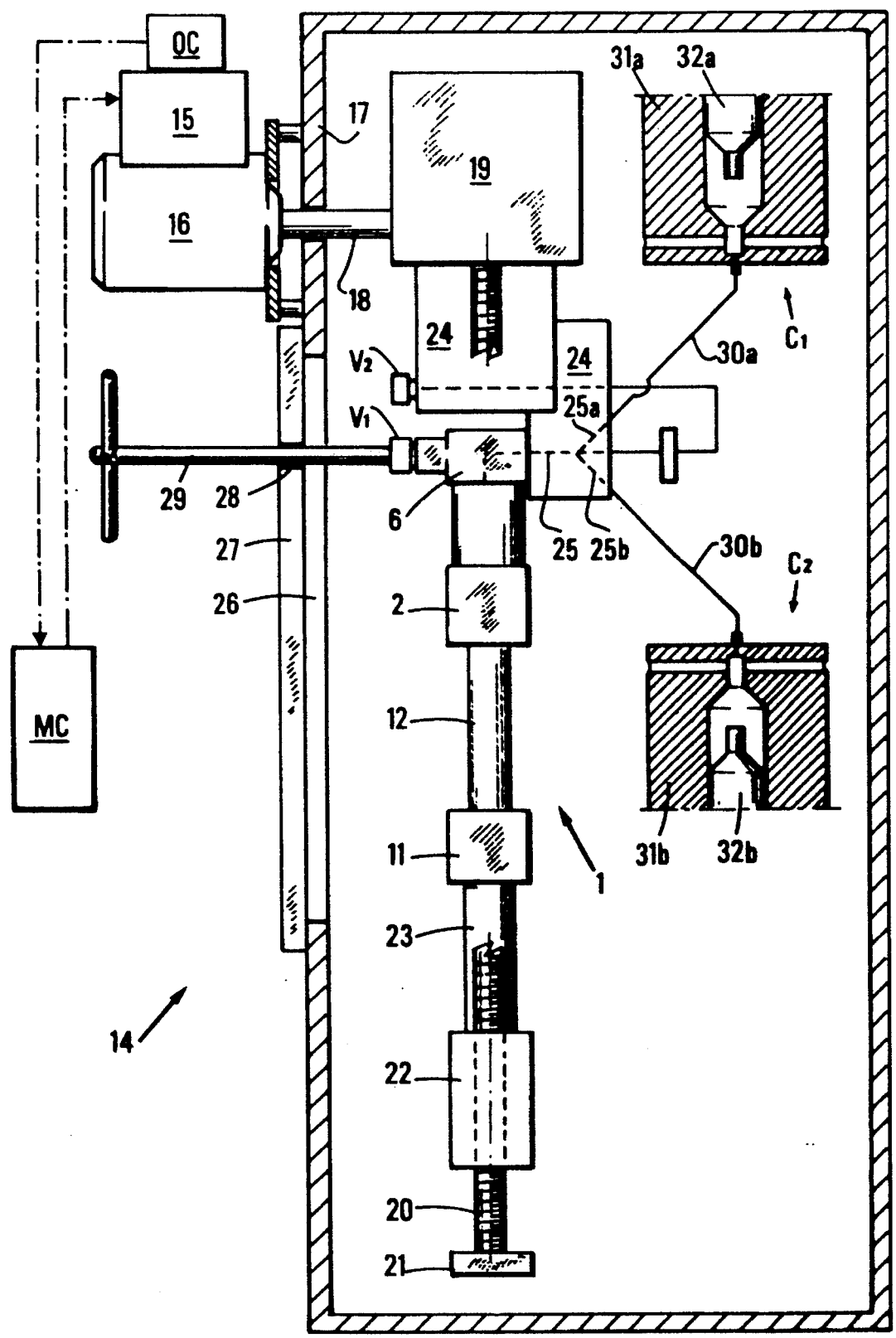
FIG. 2 diagrammatically shows the sampling cell within a thermostatically controlled enclosure.

The system includes a layout allowing easy introduction and connection of cell 1 in a thermostatically controlled enclosure 14 as illustrated in FIG. 2 whose temperature is kept, according to applications, very low (between −100° C. and −200° C. for example) or very high (from 100° C. to 200° C. for example) in order to take therein samples under high pressure, and thereafter removal from the enclosure 14.

This layout includes an electric motor 15 (FIG. 2) associated with a geared motor 16 which is fastened to the wall 17 of thermostat-controlled enclosure 14 and outside the latter. The shaft 18 of the geared motor is connected to a transmission block 19 fixed inside the thermostat-controlled enclosure. By means of gears (not shown), shaft 18 drives into rotation two threaded rods 20A and 20B (FIG. 3) arranged vertically and resting on two fixed shoes 21A, 21B. A plate 22 is provided with two threaded bores allowing passage of the two threaded rods 20 through plate 22. Rotating the rods with the shaft 18 and transmission block 19 has the effect of raising or of lowering plate 22. A piston 23 is integral with the upper face of plate 22.

The face of the head 6 of cell 1, into which channel 8 opens, rests against a connection element 24 which includes threaded holes containing to fastening screws 7. Element 24 includes an inner channel 25 communicating with two lateral channels 25A, 25B, with this communication being controlled by a neddle valve V2. By means of gears (not shown), the control of valve V2 is on the same side as the control of valve V1, opposite the wall 17 of the thermostat-controlled enclosure where an opening 26 has been provided with dimensions (about 15 cm in diameter for example) sufficient to allow the sampling cell 1 to be introduced therethrough into the thermostat-controlled enclosure and fastened to connection element 24 through tightening of screws 7 (FIG. 1) from the outside by means of spanners. A removable panel 27 closes this opening 26. Passages 28 are provided in panel 27, through which keys 29 controlling valves V1 and V2 may be engaged from outside. When the sampling cell 1 is in place against connection element 24, piston 23 (FIG. 3) is then below flange 11 and it may thus be brought in contact therewith. Actuation of motors 15, 16, and rod 20 allows piston 4 to be moved and the volume of the inner cavity 3 of sampling cell 1 to be varied.

An optical coder OC of a well-known type is associated with motor 15 and allows the linear displacements of the piston 3 of sampling cell 1 to be determined with precision. Signals indicative of the displacement are transmitted to a control microcomputer MC programmed for controlling the sampling operations.

Two tubes 30A, 30B linked for example to two substantially identical balancing cells C1, C2 of the type described for example in patent FR-2,666,415 filed by the assignee are connected to the two lateral channels 25A and 25B of connection element 24.

Each one of cells C1, C2 shown in FIG. 2 has a rigid body 31A, 31B provided with an axial cylindrical cavity for a piston 32A, 32B which may tightly slide in the cavity, motive means (not shown) for moving piston 32 in the cavity and means (not shown) for detecting the effective displacements of the two pistons. The motive means of the two balancing cells are under the control of microcomputer MC which may, according to the operations to be performed, control a separate displacement of the two pistons or a synchronized displacement thereof, the recoil of one being accompanied by the retreat of the other.

An operation of sampling of a fluid contained in the (or the two) balancing cell(s) C1, C2 comprises the following stages:

1) the sampling cell 1 being emptied through the plunging of its piston 4, cover 27 (FIG. 2) is removed and head 6 is screwed against connection element 24, by means of keys 29, by compressing O seal ring 10, Valves V1 and V2 are in closed position, 2) piston 23 is brought in contact with flange 11 and panel 27 is closed again so that the sampling cell is brought to the temperature of the thermostat-controlled enclosure, 3) valves V1 and V2 are opened so as to communicate sampling cell 1 with one (or each) of the balancing cells C1, C2, 4) under control of microcomputer MC, the synchronized displacement of rod 23 and of the piston 32A, 32B of each cell C1, C2 where fluid is to be sampled is controlled, so as to keep the overall volume of the fluid constant. The rate flow is low enough for the pressure difference between sampling cell 1 and cells C1, C2 to be negligible. With cell disassemble cell 1 being at the same temperature as cells C1, C2, sampling is achieved at the actual temperature and pressure of the fluid to be analyzed. The volume taken is obtained by multiplying the displacement of piston 4 (FIG. 1) by the section of cavity 3 and by adding the clearance volume previously calibrated under pressure, 5) in order to make sure that the sample is really representative, several synchronized up-and-down strokes of pistons 4, 32A, 32B may be controlled, 6) valve V1 is closed and the recoil of piston 4 is recorded by means of the displacement optical coder OC, 7) the withdrawal of rod 23 is controlled so as to let piston 4 take a piston of recoil against washers 13 (FIG. 2). At this stage, it may be checked that valve V1 closes properly since, otherwise, a pressure decline would appear in cells C1 or C2, 8) valve V2 is closed, and 9) panel 27 is opened and, by means of suitable keys 29, screws 7 are unscrewed so as to disunite cell CP(1) from connection element 24 and to extract it from the thermostatically controlled enclosure 14 by means of operating pliers.

The sampling cell is weighed with an analytical balance to obtain the weight difference Δp with respect to the empty cell. The moderate weight of the cell, of the order of a few hundred grams, allows analytical balances to be used, Δp being thus obtained with an accuracy greater than one milligram. By denoting the volume of the sample in the sampling conditions by V, the volume in the weighing conditions (i.e. resting against washers 13 (FIG. 1) by V', the density of air during weighing by $\rho_a$ and the acceleration of gravity by g, the density of the fluid in the sampling conditions is obtained through the relation:

$$\rho f = \frac{\Delta p + \rho_a g V'}{gV}$$

which is valid by the fact that the clearance volume (in channel 8) is low with respect to V and V' and that the empty cell is weighed with the minimum volume.

When the density is measured, the sample may be either sent back into balancing cell C1 or C2 by setting the sampling cell on connection element 24 again, or expanded in order to be analyzed in the recovery device described hereafter.

Figure 3:
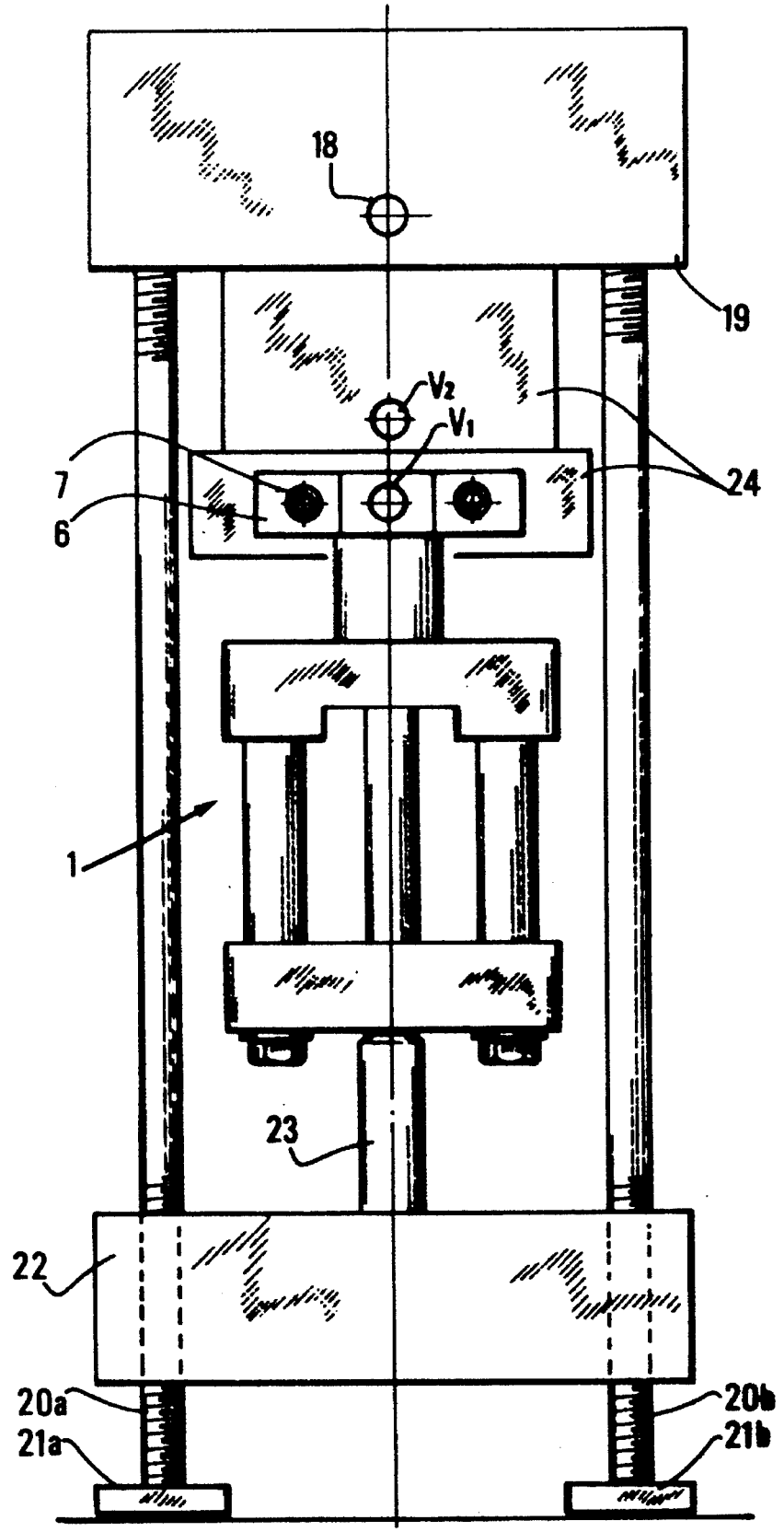
FIG. 3 diagrammatically shows an embodiment of a layout allowing fluid sampling to be controlled from outside the thermostat-controlled enclosure.
Figure 4:
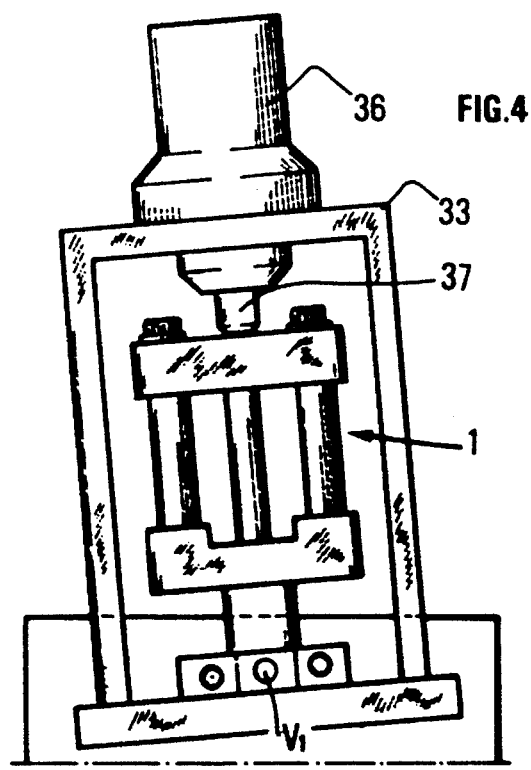
FIG. 4 diagrammatically shows an embodiment of a system for operating the sampling cell outside the thermostat-controlled enclosure.
Figure 5:
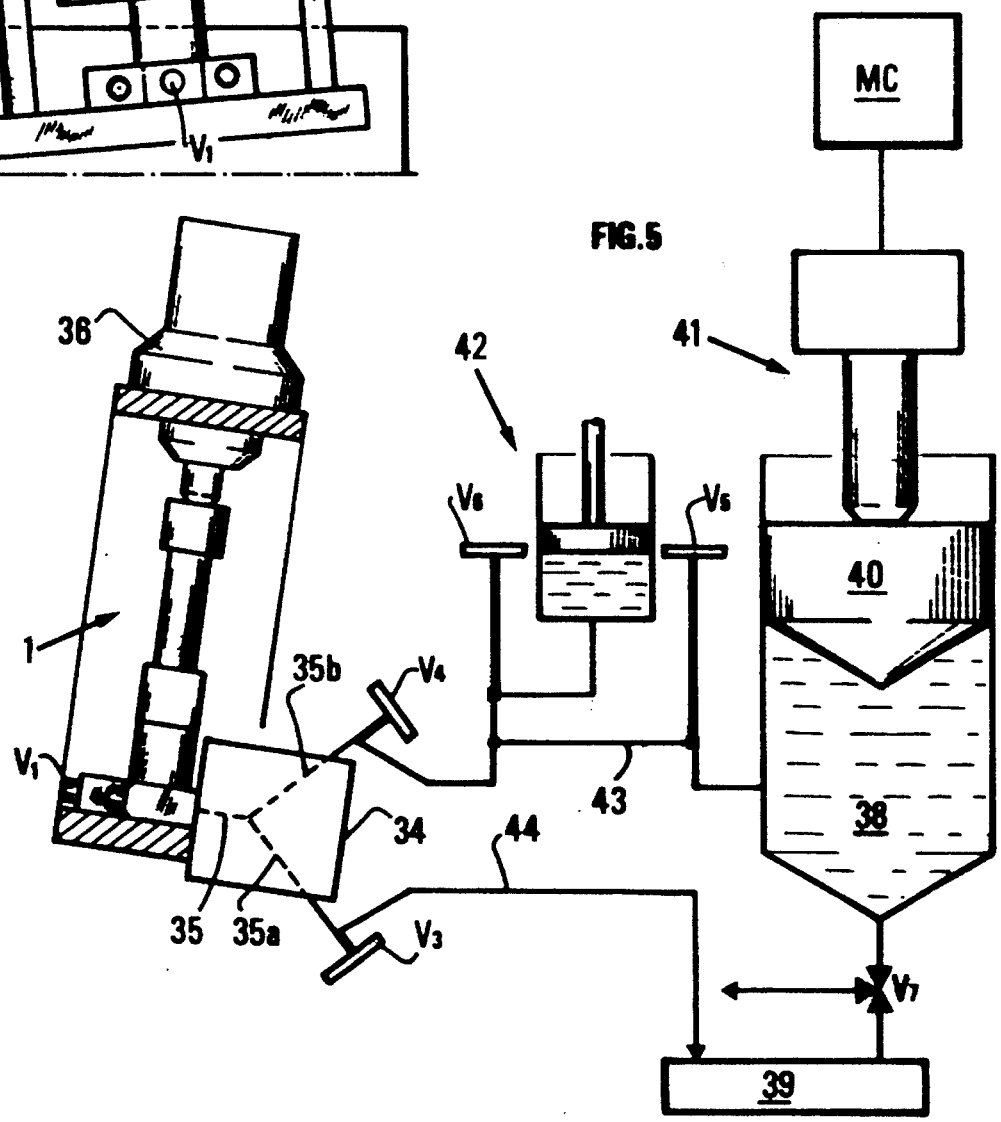
FIG. 5 diagrammatically shows a fluid reception and analysis device.

The recovery device (FIG. 4) includes an operating device comprising a rigid frame 33 associated, at the base thereof, with a connection element 34 analogous to element 24 (FIG. 2). This element 34 includes (FIG. 5) a channel 35 communicating with two lateral channels 35A, 35B controlled respectively by two valves V3, V4. Channel 35 is in alignment with the bent channel 8 of sampling cell 1 when the latter is set in contact with connection element 34 and fastened thereto by screws 7 (FIG. 3). A pneumatic jack 36 having rod 37 resting against the flange 11 of sampling cell 1 is fastened to frame 33. Jack 36 is connected to a source of compressed air which is not shown. Actuating jack 36 allows the fluid to be totally discharged from cell 1 except for the clearance volume. The recovery device is inclinable (FIG. 5) so as to facilitate the total discharge of the fluid from sampling cell 1.

By means of valve V3, channel 35A communicates with a line 44 linked to a separating bottle 39, which communicates with a gasometer 38 via an access valve V7. The gasometer, of a well-known type, includes a chamber defined by a piston 40 having a volume modified through the action of control operated actuator 41 controlled by microcomputer MC so as to keep the inner volume of gasometer 38 at a pressure lower than or equal to a set value.

The recovery device further includes a solvent injection element 42, which is connected to a line 43 communicating through a valve V5 with the gasometer and through a valve V6 with the channel 35B of connection element 34.

Gasometer 38 and separating bottle 39 may be communicated with a vacuum pump (not shown) by connecting the latter to line 43 instead of injection element 42.

The operations of expansion and of analysis of the sample taken are performed as follows:

Before expanding the sample, the entire separating bottle 39 and of gasometer 38 is placed under vacuum by opening valve V7, and the piston 40 of the gasometer is set in a position where the volume thereof is greater than the expected gas volume. Expansion is obtained by gently opening valve V3 so that the sample does not enter separating bottle 39 at too high a speed which might cause liquid droplets to be carried over into gasometer 38.

Instead of evacuating the bottle-gasometer assembly before expanding the sample, it is also possible to fill this assembly with an inert gas under atmospheric pressure, which is a priori known not to be part of the mixture (helium for example). A suitable correction allows the volume of gas due to the sample to be obtained. The analysis is not modified by the presence of this inert gas.

During the expansion of the sample, separating bottle 39 is kept at a very low temperature through immersion in liquid nitrogen, in order to promote the trapping of the condensable gases and of the liquids in the bottle. When expansion is completed, the separating bottle is let come up progressively to the ambient temperature so as to allow the vaporization of the condensable gases and of part of the volatile liquids in the gasometer. Reading of the volumes of gasometer 38 and of the volume of liquid present in bottle 39 which is graduated therefore allows the gas/liquid ratio in the set separation conditions to be determined (ambient temperature and atmospheric pressure for example). Each of the phases may be sampled by means of a syringe with a view to a chromatographic analysis, after closing separation valve V7 and disuniting separating bottle 39 from gasometer 38.

In some cases, a solvent injection is carried out in order to recover all of the sample, notably if a precipitation of the solid phases (paraffins, asphaltenes, etc) is feared, or if the volume of liquid collected in the bottle is too low for the liquid possible remaining in the clearance volumes to be disregarded.

After remounting the cell, the solvent is injected into the sampling cell by means of injection element 42, with valves V4 and V6 being open and valves V3 and V5 being closed. The piston 4 of the sampling cell is thus pushed back until it reaches the recoil position thereof. When the desired volume of solvent is injected in cell 1, valve V1 is closed in order to dismantle the cell and to weigh it. It is thus possible to known precisely the mass of solvent introduced and to promote the bringing into solution of the sample remainders through adequate stirring. When these operations are completed, cell 1 is mounted again, for the last time, on connection element 34 in order to transfer the solvent and the sample dissolved therein, by opening valve V3 and by pushing piston 4 back by means of pneumatic jack 36. This allows possible deposits present between the cell 1 separating bottle 39 to be recovered and the sample to be subjected to a quantitative analysis.

In order to minimize the amount of solvent remaining in the clearance volumes, sampling cell 1 may be heated up to a temperature higher than the boiling point of the solvent. The volume increase resulting from the vaporization of the solvent remaining in the sampling cell thus leads to a transfer of the solvent towards separating bottle 39. Particularly the liquid solvent remaining in the line between valve V1 and separating bottle 39 is driven away by the solvent vapors, which improves the recovery of the sample. The solvent vapors condense in the separating bottle which is kept at the ambient temperature. This solvent injection device is also a simple and reliable means for cleaning the cell and the recovery circuit before the next sampling.

In short, the previous operations mainly consist in:

1) after weighing separating bottle 39 empty, placing the whole of the bottle and of gasometer 38 (valves V3 and V7 are open and the other valves are closed) under vacuum or under inert gas atmosphere,
2) immersing separating bottle 39 into a cooler,
3) opening valve V1 as gently as possible,
4) actuating piston 4 in the sampling cell 1 by means of pneumatic jack 36,
5) closing valves V1 and V3, and
6) dismantling sampling cell 1 in order to weigh it.

Two cases may thus arise:

a) If the sample mass remaining in the sampling cell is negligible, the cooler vessel just has to be removed and separating bottle 39 is let come up progressively to the ambient temperature, which leads to a conventional expansion with 7a) modification of the gasometer volume in order to reach the standard pressure,
8a) closing of separation valve V7 and approximate reading of the liquid volume,
9a) chromatographic analysis of the gas, allowing the mass of gas ($m_G$) to be determined,
10a) dismantling of the separating bottle and weighing, in order to measure the mass of liquid ($m_L$) under standard conditions,
11a) checking of the balance $M_L+m_G=m_T$ where $m_T$ is the total sample mass which has been obtained by weighing sampling cell 1 prior to and after transfer,
12a) analysis of the liquid through chromatography or any other method;

b) if the sample mass remaining in the sampling cell is not negligible, a solvent in then injected according to the following procedure:

7b) reassembly of the cell,
8b) injection of solvent by means of injection element 42, valve V3 remaining closed and valves V1, V4 and V6 being open,
9b) closing of V1 and V4,
10b) dismantling of the sampling cell and weighing in order to measure the mass of solvent($m_S$),
11b) withdrawal of bottle 39 from the cooler and progressive return to the ambient temperature thereof,
12b) stirring of sampling cell 1 so as to bring the solids possibly trapped therein into solution,
13b) reassembly of sampling cell 1 and closing of separation valve V7 between gasometer 38 and separating bottle 39,
14b) opening of valves V1 and V3 and transfer of the solvent into separating bottle 39 by actuating pneumatic jack 36,
15b) heating of sampling cell 1 to a temperature higher than the boiling point of the solvent,
16b) closing of V1 and V3,
17b) chromatographic analysis of the gas in order to obtain the mass of gas ($m_G$),
18b) dismantling of the separating bottle and weighing, in order to deduce therefore the mass of solvent and the mass of sample in solution ($m_{LS}$),
19b) checking of the balance $m_{LS}+m_G=m_T+m_S$ where $m_T$ is the mass of sample obtained by weighing the cell prior to and after transfer, and
20b) analysis of the liquid (solvent+sample in solution) through gas chromatography or any other technique.

An application has been described in which the sample taken is kept at a high temperature. The sampling cell described is however also adapted for transferring samples which have been kept at a temperature lower than 0° C. (between 0° C. and −200° C. for example).

We claim:

1. A system for transferring samples of fluids to an analysis device for determining thermodynamic properties thereof, comprising:

a sampling cell for containing fluids maintained under pressure including a body provided with a head, a cavity in the body communicating with outside the sampling cell through a first channel and an opening port, a first control valve for controlling fluid flow through the first channel, a piston slidable in the cavity between a first position where the sampling cell has a minimum volume and a second adjustable position where the sampling cell has a volume larger than the minimum volume, the piston being connected to a flange slidably mounted relative to two lateral guide elements extending through the flange for guiding the piston with respect to the body;

a thermostatically controlled enclosure having a wall with opening therein;

a second control valve, a first fixed connected member disposed in the thermostatically controlled enclosure adjacent the openings, the first connection member having an inner channel for communication with at least one balancing cell through the second control valve;

a control, actuatable from outside the thermostatically controlled enclosure, for providing a controlled communication between the cavity and the first and second control valves with the first and second control valves being for providing controlled communication with the at least one balancing cell when connected thereto;

a first operating assembly including a motor outside the thermostatically controlled enclosure and a transmission driven by the motor for controlling the displacement of the piston of sampling cell; and a transfer device for controlling transfer of fluids between the sampling cell and the analysis device.

2. A system as claimed in claim 1 wherein:

the first operating assembly includes guide rods, the transmission includes a block mounted with means for rotating the guide rods, to move the block linearly to drive the piston in the cavity.

3. A system as claimed in claim 1 wherein:

the second valve has an actuation element permitting control from outside the thermostatically controlled enclosure through the openings.

4. A system as claimed in claim 2 wherein:

the second valve has an actuation element permitting control from outside the thermostatically controlled enclosure through the openings.

5. A system as claimed in claim 1 further comprising:

the analysis device; and wherein the transfer device includes a second operating assembly including a support for fastening the head to the second operating assembly, at least one valve for controlling transfer of fluids between the sampling cell and the analysis device and means abutting against the piston for driving the piston.

6. A system as claimed in claim 2 further comprising:

the analysis device; and wherein the transfer device includes a second operating assembly including a support for fastening the head to the second operating assembly, at least one valve for controlling transfer of fluids between the sampling cell and the analysis device and means abutting against the piston for driving the piston.

7. A system as claimed in claim 5 further comprising:

the analysis device, a second connection element; and a solvent injection element, and wherein the second connection element includes at least a third valve for controlling communication between the sampling cell and the solvent injection element, and the transfer device further includes at least one fourth valve for controlling transfer of fluid between the solvent injection element, the sampling cell and the analysis device.

8. A system as claimed in claim 6 further comprising:

the analysis device, a second connection element and a solvent injection element; and wherein the second connection element includes at least a third valve for controlling communication between the sampling cell and the solvent injection element, and the transfer device further includes at least one fourth valve for controlling transfer of fluid between the solvent injection element, the sampling cell and the analysis device.

9. A system as claimed in claim 5 further comprising:

the analysis device; and wherein the analysis device includes a gasometer, a separating bottle, and the system includes a fifth valve for controlling communication between the gasometer and a vacuum pump.

10. A system as claimed in claim 6 further comprising:

the analysis device; and wherein the analysis device includes a gasometer, a separating bottle, and the system includes a fifth valve for controlling communication between the gasometer and a vacuum pump.

11. A system as claimed in claim 1 wherein:

the control includes keys for operating the first and second valves through the openings in the wall of the thermostatically controlled enclosure.

12. A system as claimed in claim 2 wherein:

the control includes keys for operating the first and second valves through the openings in the wall of the thermostatically controlled enclosure.

13. A system as claimed in claim 1 comprising:

a control processor for controlling operation of the first operating assembly.

14. A system as claimed in claim 2 comprising:

a control processor for controlling operation of the first operating assembly.

15. A system as claimed in claim 13 wherein:

the control processor includes means for synchronizing transfer of fluid at a substantially constant pressure between the at least one balancing cell and the sampling cell.

16. A system as claimed in claim 14 wherein:

the control processor includes means for synchronizing transfer of fluid at a substantially constant pressure between the at least one balancing cell and the sampling cell.

17. A system as claimed in claim 5 further comprising:

a control processor including means for synchronizing transfer of fluid between the sampling cell when coupled with the second operating assembly and the analysis device.

18. A system as claimed in claim 6 further comprising:

a control processor including means for synchronizing transfer of fluid between the sampling cell when coupled with the second operating assembly and the analysis device.

19. A system as claimed in claim 1 wherein:

the first valve is a needle valve positioned so that a clearance volume in the first channel between the cavity in the first position of the piston and the port is at a minimum.

20. A system as claimed in claim 2 wherein:

the first valve is a needle valve positioned so that a clearance volume in the first channel between the cavity in the first position of the piston and the port is at a minimum.

21. A system as claimed in claim 1 further comprising:

optical coder, coupled to the motor, for sensing displacement of the piston caused by operation of the motor.

22. A system as claimed in claim 2 further comprising:

optical coder coupled to the motor, for sensing displacement of the piston caused by operation of the motor.

* * * * *